(12) United States Patent
Lewis et al.

(10) Patent No.: US 11,638,811 B2
(45) Date of Patent: May 2, 2023

(54) PERCUTANEOUS ACCESS APPARATUS

(71) Applicant: RENISHAW PLC, Wotton-under-Edge (GB)

(72) Inventors: Trefor Owen Lewis, Bristol (GB); Patricia Grace Stewart, Bristol (GB)

(73) Assignee: RENISHAW PLC, Wotton-under-Edge (GB)

( * ) Notice: Subject to any disclaimer, the term of this patent is extended or adjusted under 35 U.S.C. 154(b) by 0 days.

(21) Appl. No.: 16/097,780

(22) PCT Filed: May 10, 2017

(86) PCT No.: PCT/GB2017/051293
§ 371 (c)(1),
(2) Date: Oct. 30, 2018

(87) PCT Pub. No.: WO2017/194933
PCT Pub. Date: Nov. 16, 2017

(65) Prior Publication Data
US 2019/0167964 A1      Jun. 6, 2019

(30) Foreign Application Priority Data

May 12, 2016   (EP) ..................................... 16169472

(51) Int. Cl.
*A61M 39/02* (2006.01)
*A61M 39/04* (2006.01)
(Continued)

(52) U.S. Cl.
CPC ........ *A61M 39/0247* (2013.01); *A61M 39/04* (2013.01); *A61M 39/105* (2013.01);
(Continued)

(58) Field of Classification Search
CPC ............ A61M 39/0247; A61M 39/105; A61M 39/04; A61M 2039/0264;
(Continued)

(56) References Cited

U.S. PATENT DOCUMENTS 4,315,513 A * 2/1982 Nawash ............... A61J 15/0015
604/151
4,581,020 A * 4/1986 Mittleman ........ A61M 39/0247
604/175
(Continued)

FOREIGN PATENT DOCUMENTS

EP       1 426 074 A1     6/2004
EP       1426074 A1 *     6/2004    ............ A61M 39/02
(Continued)

OTHER PUBLICATIONS

Nov. 4, 2016 Search Report and Written Opinion issued in European Patent Application No. 16 169 472.4.
(Continued)

*Primary Examiner* — Tiffany Legette
*Assistant Examiner* — Avery Smale
(74) *Attorney, Agent, or Firm* — Oliff PLC

(57) ABSTRACT

A percutaneous fluid access apparatus includes a percutaneous fluid access device. The percutaneous fluid access device has a base portion including a subcutaneous portion and at least one port for connection to one or more fluid conduits within a body of a patient. A housing has at least one fluid channel and at least one seal for sealing the at least one fluid channel, and the housing is removably attachable
(Continued)

to the base portion. The at least one fluid channel is in fluid communication with the at least one port when the housing is attached to the base portion.

16 Claims, 8 Drawing Sheets

(51) Int. Cl.
*A61M 39/10* (2006.01)
*A61M 39/08* (2006.01)
*A61M 39/00* (2006.01)

(52) U.S. Cl.
CPC ............. *A61M 2039/0081* (2013.01); *A61M 2039/0205* (2013.01); *A61M 2039/025* (2013.01); *A61M 2039/027* (2013.01); *A61M 2039/0261* (2013.01); *A61M 2039/0264* (2013.01); *A61M 2039/0276* (2013.01); *A61M 2039/0282* (2013.01); *A61M 2039/0288* (2013.01); *A61M 2039/082* (2013.01); *A61M 2205/12* (2013.01); *A61M 2207/00* (2013.01); *A61M 2210/0687* (2013.01); *A61M 2210/0693* (2013.01)

(58) Field of Classification Search
CPC .. A61M 2039/0282; A61M 2039/0288; A61M 2039/0081; A61M 2039/0205; A61M 2039/025; A61M 2039/027; A61M 2039/0276; A61M 2039/082; A61M 2039/0258; A61M 2039/0291; A61M 2210/0693
See application file for complete search history.

(56) References Cited

U.S. PATENT DOCUMENTS

| | | |
|---|---|---|
| 4,790,826 A | 12/1988 | Elftman |
| 4,804,369 A * | 2/1989 | Lapeyre ............ A61M 39/0247 |
| | | 604/175 |
| 5,147,321 A | 9/1992 | Slonina et al. |
| 6,609,020 B2 | 8/2003 | Gill |
| 7,329,262 B2 | 2/2008 | Gill |
| 8,827,987 B2 | 9/2014 | Fielder et al. |
| 8,974,422 B2 | 3/2015 | Gill et al. |
| 9,174,037 B2 | 11/2015 | Schutz et al. |
| 2002/0183604 A1 | 12/2002 | Gowda et al. |
| 2015/0018799 A1* | 1/2015 | Lewis ................. A61M 5/142 |
| | | 604/533 |

FOREIGN PATENT DOCUMENTS

| | | | |
|---|---|---|---|
| WO | 87/07509 A1 | 12/1987 | |
| WO | 03/077785 A1 | 9/2003 | |
| WO | 2011/150978 A1 | 12/2011 | |
| WO | WO-2011150978 A1 * | 12/2011 | .......... A61M 39/285 |
| WO | 2013/117659 A2 | 8/2013 | |
| WO | 2013/117661 A2 | 8/2013 | |

OTHER PUBLICATIONS

Jul. 27, 2017 International Search Report issued in International Patent Application No. PCT/GB2017/051293.

Jul. 27, 2017 Written Opinion of the International Searching Authority issued in International Patent Application No. PCT/GB2017/051293.

* cited by examiner

PERCUTANEOUS ACCESS APPARATUS

This application is a national stage application of International Application No. PCT/GB2017/051293, filed May 10, 2017, which in turn claims priority to European Patent Application No. 16169472.4, filed May 12, 2016.

FIELD OF THE INVENTION

The present invention relates to medical apparatus and in particular percutaneous access apparatus for delivering fluids, such as drugs, to different parts of the human or animal body, such as the brain.

BACKGROUND OF THE INVENTION

The drug treatment of a number of neuro-degenerative disorders, hereditary neurological disorders, brain tumours and other diseases of the nervous system are compromised by the presence of the blood brain barrier which prevents the transfer of drugs from the vascular system or cerebrospinal fluid into the brain substance. Examples of drugs which do not adequately cross the blood brain barrier include protein molecules such as neurotrophins, monoclonal antibodies, viral particles for delivery of gene therapy, as well as a number of cytotoxic drugs for the treatment of tumours. It has been described previously how such drugs can be delivered to the brain by direct infusion into the parenchyma via one or more indwelling catheter. For example, a guide tube and catheter system is described in U.S. Pat. No. 6,609,020. A catheter with a small external diameter that can be precisely positioned in the brain is described in WO2003/077785.

Percutaneous access apparatus is described in WO2013/117659, including a percutaneous fluid access device, which is anchored directly to the skull of the patient and provides a fluidic link to subcutaneously implanted catheters. Fluid is transferred via needles inserted through a septum into fluid channels in the percutaneous fluid access device. The fluid channels connect the fluid pathway to the catheter system, and the septum provides a seal to the fluid channels. Repeated insertion of the needles though the septum leads to degradation of the septum.

More generally, filters, septa, etc. of percutaneous access apparatus can require periodic replacement.

Replacement of the septum and any associated filters occurs under surgical conditions in an aseptic environment. This can require repeated surgery, and is undesirable since the patient is then exposed to the additional risk associated with surgery, such as infection, complications etc.

SUMMARY OF THE INVENTION

A first aspect of the invention provides a percutaneous fluid access apparatus including: a percutaneous fluid access device comprising a base portion including a subcutaneous portion and at least one port for connection to one or more fluid conduits within a body of a patient, and a housing comprising at least one fluid channel and at least one seal for sealing the at least one fluid channel, wherein the housing is removably attachable to the base portion, and the at least one fluid channel is in fluid communication with the at least one port when the housing is attached to the base portion.

A further aspect of the invention provides a method of using a percutaneous fluid access apparatus comprising a percutaneous fluid access device including a base portion including a subcutaneous portion and at least one port for connection to one or more fluid conduits within a body of a patient, and a housing comprising at least one fluid channel and at least one seal for sealing the at least one fluid channel, wherein the housing is removably attachable to the base portion, and the at least one fluid channel is in fluid communication with the at least one port when the housing is attached to the base portion, the method including the step of: removing the housing from the percutaneous fluid access device.

The invention is advantageous in that the housing containing the seal can be easily replaced from the external side of the port (ideally without disturbing the skin interface). The housing would normally be secured in place to the base portion to stop it separating inadvertently. Since the skin interface is not disturbed (or only minimally) the housing and associated seal can preferably be replaced in a healthcare environment but outside of a surgical environment.

The seal may be a septum or other seal for sealing the one or more fluid channels.

The base portion may have an extracorporeal surface, wherein the housing is removably attachable to the extracorporeal surface. The housing may be entirely extracorporeal and located entirely above the extracorporeal surface when attached to the base portion.

Alternatively, the base portion may have a subcutaneous surface, wherein the housing is removably attachable to the subcutaneous surface. The subcutaneous surface would sit below the upper layer of surrounding tissue but the base portion may have one or more side walls around the subcutaneous attachment surface that extend up to or beyond the upper layer of surrounding tissue. The subcutaneous surface in this arrangement is not itself directly beneath tissue but is below the level of the locally surrounding tissue. The housing may be located partially above and partially below the surrounding tissue. In this arrangement it may sometimes be necessary to break the surrounding tissue to remove the housing.

In a further alternative arrangement the base portion may have an extracorporeal surface and a recess, wherein the housing is adapted to be inserted into the recess through the extracorporeal surface. The recess (and therefore the housing, when installed in the recess) may extend subcutaneously, or may be percutaneous, or may be entirely extracorporeal.

The housing may further comprise at least one filter in the least one fluid channel. The filter may be a particle, bacterial and/or air filter. The filter may be arranged to catches small pieces of the seal or septum, e.g. released when the septum is penetrated by a needle. Removal of the housing from the base portion may remove the one or more seals and the one or more filters contained within.

The housing, including the seal(s), filter(s) etc. contained therein may be disposable after removal from the base portion. Alternatively it may be desirable that one or more parts of the housing are replaceable. For example, the seal/septum and/or the filter may be separable from the housing after removal from the base portion.

When the housing is installed on the base portion, the filter is preferably located between the seal and the port.

The housing may include a plurality of fluid channels. Each fluid channel may be sealed by a respective seal (or septum), or multiple or all of the fluid channels may be sealed by one or more septa. Each fluid channel may include a respective filter, or multiple or all of the fluid channels may be associated with one or more filters.

The percutaneous fluid access apparatus may further comprise a cap, wherein the housing is between the base and the cap. The cap may retain the housing in the recess. The housing may alternatively be press fit in the recess. The cap may include one or more apertures through which the one or more seals of the housing are accessible extracorporeally.

The percutaneous fluid access apparatus may further comprise a connector device having at least one fluid duct, wherein the connector device is adapted for connection to the percutaneous fluid access device to establish fluid communication between the at least one fluid duct and the at least one fluid channel.

The connector device may have a plurality of fluid ducts, and the percutaneous fluid access device may have a corresponding plurality of fluid channels.

The connector device may include one or more hollow needles, which define wholly or in part the one or more fluid ducts. The one or more hollow needles may be configured to be inserted through the at least one septum/seal of the housing to establish fluid communication between the one or more fluid ducts and the one or more ports of the base portion.

Alternatively, the connector device may be needleless. In a needleless arrangement the one or more ducts of the connector device may be configured to fluidically connect with the one or more fluid channels in the housing upon connection of the connector device to the percutaneous fluid access device.

The connector device may include one or more seals for fluidically sealing the one or more ducts.

The connector device may be required to be removed from the percutaneous fluid access device before the housing can be separated from the base portion of the percutaneous fluid access device. Prior to removal of the connector device it may be required to remove the one or more hollow needles of the connector device through the seal/septum to disestablish fluid communication between the one or more hollow needles and the one or more fluid channels. A connector device may also be attached to the housing during removal of the housing from the base portion. A connector device may be attached to the housing during connection of the housing to the base portion. The connector device may allow air to be vented to atmosphere during removal and/or attachment.

The at least one port may be connected to one or more fluid conduits in the form of one or more catheters. The catheters may be neurosurgical (e.g. intraparenchymal) catheters. The percutaneous fluid access apparatus may comprise one or more fluid conduits (such as one or more catheters).

The percutaneous fluid access apparatus may further comprise a cover adapted to fit over the base portion when the housing is removed from the base portion. The cover may be arranged to seal the one or more ports of the base portion.

The percutaneous fluid access apparatus may further comprise a tool adapted to engage the base portion and the housing during removal and/or assembly of the housing to/from the base portion. The tool may be arranged to bear against the base portion and the housing caused to exert a force between the base portion and the housing without significant force being imparted from the base portion to the patient.

At least one second seal may be provided between the housing and the base portion. The second seal may provide a debris and/or fluid seal.

The base portion may have at least one third seal for sealing the at least one port upon removal of the housing from the base portion. Alternatively or additionally, the base portion may include at least one membrane that prevents the ingress of air.

The base portion may include at least two ports. The housing may include at least two fluid channels. The base portion may include more than two ports. The housing may include more than two fluid channels. The base portion may include four or more ports. The housing may include four or more fluid channels. Each port may be connected to a fluid conduit (e.g. in the form of a catheter). A plurality of catheters (e.g. at least two catheters, more than two catheters or four or more catheters) may thus be provided.

After removal of the housing from the percutaneous fluid access device, the method may include attachment of a replacement or refurbished housing to the percutaneous fluid access device. In refurbishment of the housing, the one or more seals and/or the one or more filters may be removed from the housing and one or more new seals and/or one or more new filters may be inserted in the housing.

The method may take place in an aseptic environment.

The method may not be a step in a surgical procedure.

BRIEF DESCRIPTION OF THE DRAWINGS

Embodiments of the invention will now be described with reference to the accompanying drawings, in which.

DETAILED DESCRIPTION OF
EMBODIMENT(S)

Figure 1:
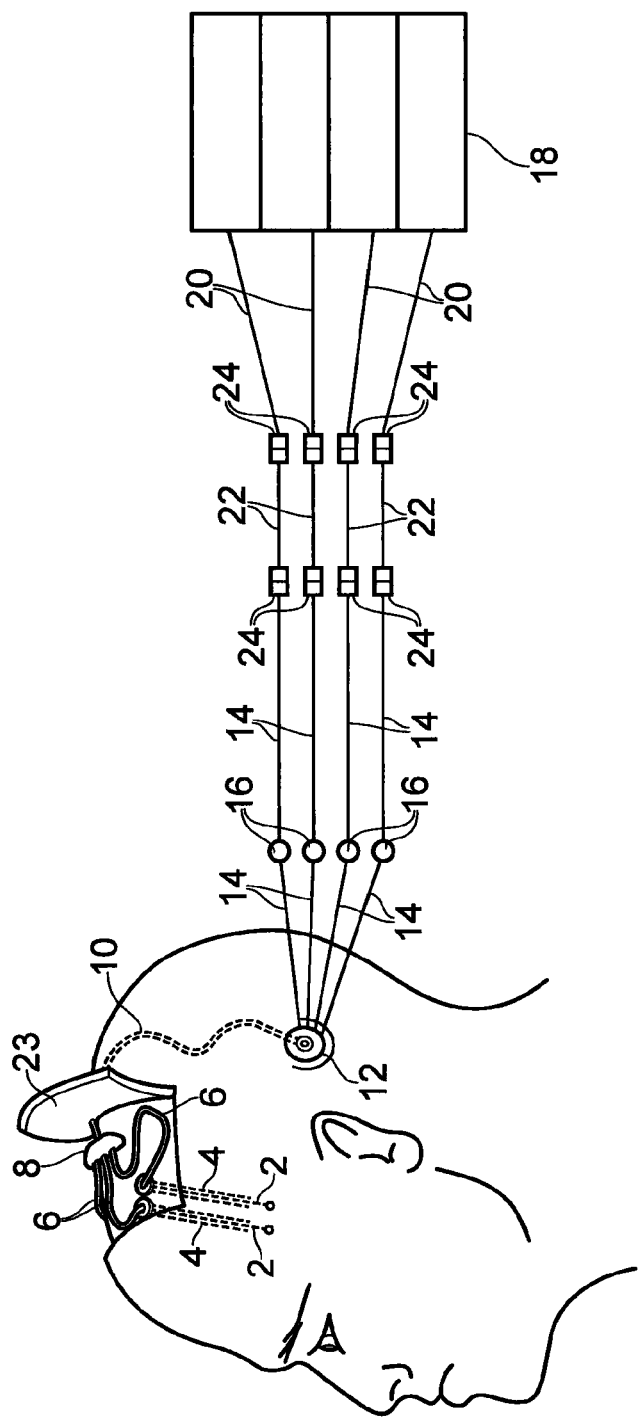
FIG. 1 shows a drug delivery system including a percutaneous fluid access device for delivery of a drug to the brain of a patient.

Referring to FIG. 1, an overview of the apparatus for delivering fluid to the brain is illustrated when implanted in a subject.

The apparatus comprises four fine catheters 2, each catheter being inserted into the brain via a previously implanted guide tube 4 (although it should be noted that only two of these are shown in FIG. 1). Suitable stereotactic insertion apparatus and methods have been described elsewhere previously, for example see U.S. Pat. No. 7,329,262 for details of a stereoguide based catheter insertion procedure. Supply tubing 6 runs from each catheter 2 to a hub 8. The hub 8 is connected by a length of multi-lumen tubing 10 to percutaneous access apparatus 12. The catheters 2, guide tubes 4, supply tubing 6, hub 8 and multi-lumen tubing 10 are all subcutaneously implantable (i.e. buried beneath the skin of the patient).

The percutaneous access apparatus 12 comprises a percutaneous fluid access device that is anchored directly to the skull of the patient. The percutaneous fluid access device comprises an extracorporeal portion to which an associated connector device is releasably attached. The percutaneous access apparatus 12 thus enables a fluidic link to the implanted catheters 2 to be established when required. In particular, the arrangement provides a separate, isolated, fluidic pathway to each catheter 2. More details about the percutaneous access apparatus 12 are provided below.

Outside of the body, the connector device of the percutaneous access apparatus 12 is linked to four external supply tubes 14. Each supply tube 14 includes an in-line bacterial and/or air filter 16. A four channel syringe pump 18 (which may comprise four separate single channel syringe pumps) is also provided. An outlet tube 20 from each channel of the syringe pump 18 is linked to one of the external supply tubes 14 via a drug storage tube 22. As will be explained in more detail below, each drug storage tube 22 is preloaded with a desired volume of therapeutic agent allowing the syringe pump 18 to be loaded with an inert solution (e.g. saline or artificial CSF). Fluidic connections between the drug storage tube 22 and the outlet tubes 20 and supply tubes 14 are made using low dead volume Luer lock connectors 24.

In use, the catheters 2, guide tubes 4, supply tubing 6, hub 8 and multi-lumen tubing 10 are all subcutaneously implanted in the subject (i.e. the skin flap 23 showed in a raised position in FIG. 1 is folded down and sutured in place). The percutaneous fluid access device of the percutaneous access apparatus 12 is also secured in place (e.g. attached to the skull and left protruding through the scalp) thereby providing the required fluid connection as and when required. These components are preferably suitable for long term implantation within a subject. For example, they may be designed to remain implanted for months or years.

When delivery of therapeutic agent is required, a connector device is attached to the percutaneous fluid access device. The supply tubes 14 (pre-primed with inert fluid) are then connected to the syringe pump via drug storage tubes 22 that contain the required dosage of therapeutic agent that is to be delivered. Each channel of the syringe pump is arranged to expel inert fluid (saline, artificial CSF etc) thereby pushing the therapeutic agent through the apparatus and expelling it from the tips of each catheter 2. The rate of fluid flow can be precisely controlled using the syringe pump 18 and the amount of therapeutic agent can be precisely set by defining the volume of the drug storage tubes 22. It is possible for fluid delivery to be continuous or intermittent. Fluid may also be delivered through all, or just some, of the catheters in parallel and/or it may be delivered sequentially through a sub-set of one or more catheters in turn. The precise delivery protocol can be set by a clinician.

FIGS. 2 and 3 describe two embodiments of the percutaneous fluid access device 100 that forms part of the percutaneous access apparatus 12 of FIG. 1.

Figure 2A:
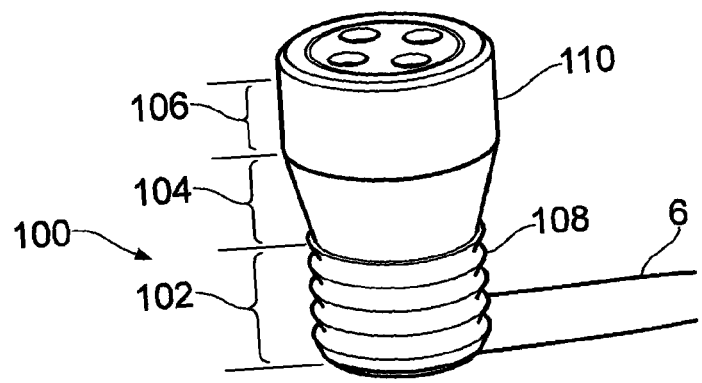
FIG. 2a is a perspective view of an embodiment of a percutaneous fluid access device for a percutaneous fluid access apparatus.
Figure 2B:
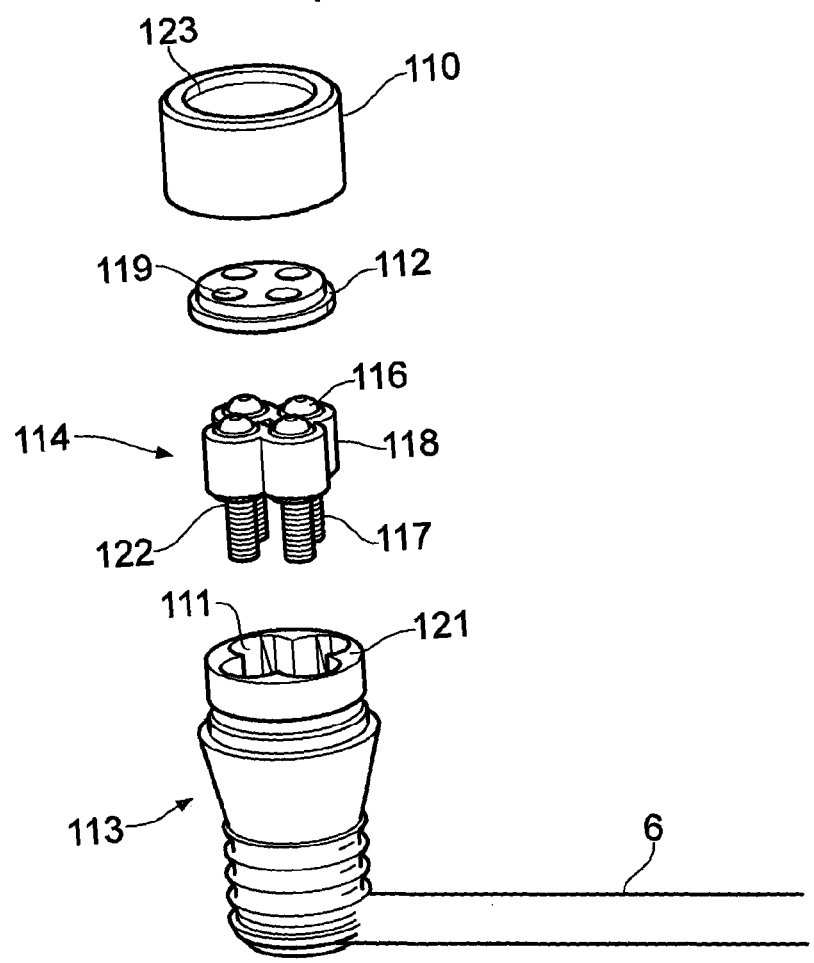
FIG. 2b is an exploded perspective view of the percutaneous fluid access device of FIG. 2a, FIG. 2c is a cross sectional view of the embodiment of the percutaneous fluid access device of FIGS. 2a and 2b.
Figure 2C:
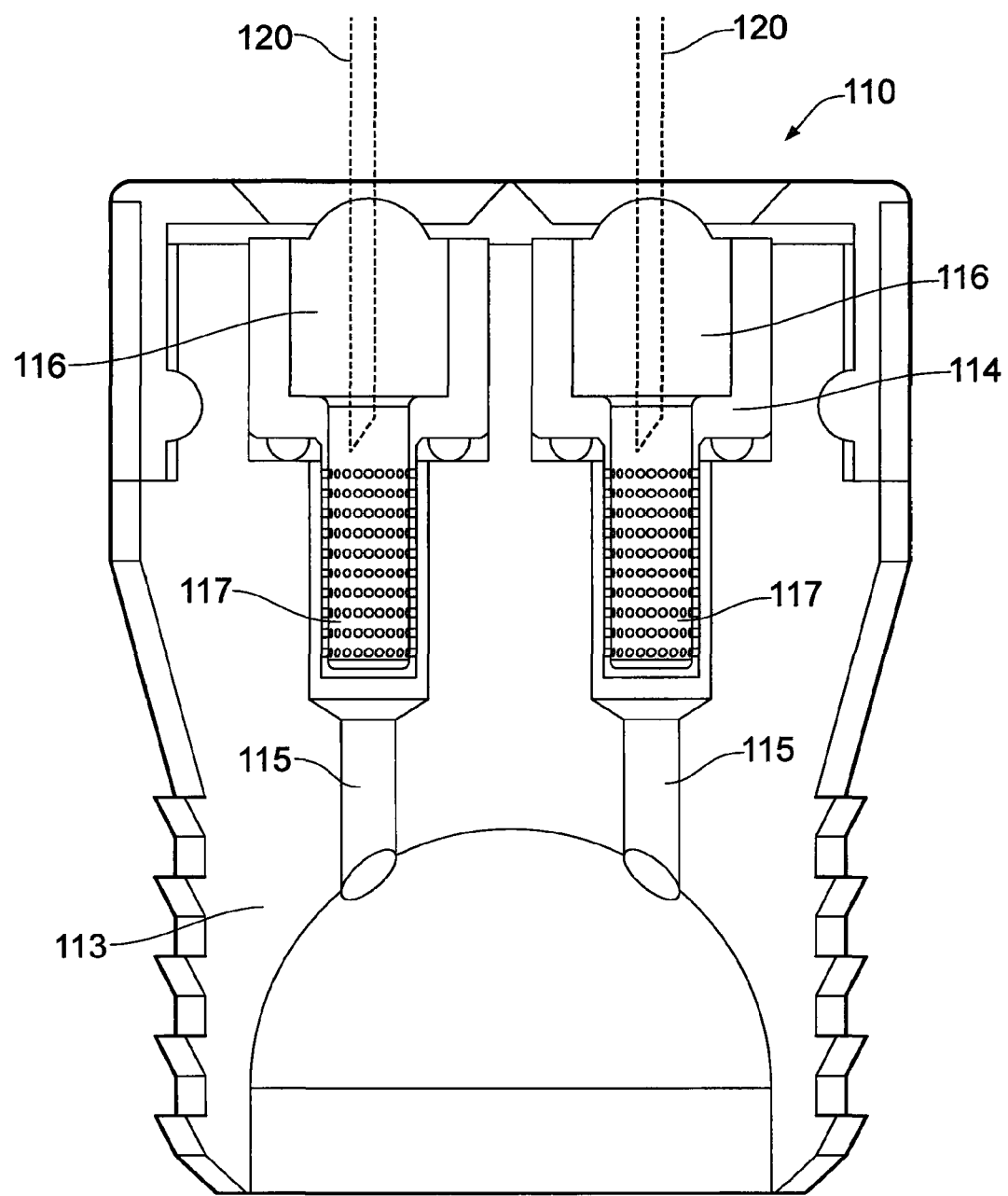

In the embodiment shown in FIGS. 2a, 2b and 2c, the percutaneous fluid access device 100 comprises a subcutaneous portion 102, a percutaneous portion 104 and an extracorporeal portion 106.

The subcutaneous portion 102 is substantially cylindrical with protruding ribs 108 that enable secure attachment of the device to a hole formed in the skull via an interference or press fit. Alternatively, the subcutaneous portion 102 can be secured to the skull via plates that may be fixed via screws (or by any other suitable fixing method) into the skull. The external surface of the subcutaneous portion 102 is also roughened to promote osseointegration after implantation. The ribs 108 have an inclined surface that is at an angle of between around 15 and 35 degrees to the longitudinal axis; this helps retain the device securely in place after implantation.

The percutaneous portion 104 (which can also be termed a transcutaneous portion) is the part of the device that passes through the skin. The surface of the percutaneous portion 104 is also roughened to promote skin in-growth after implantation thereby reducing the risk of infection. The percutaneous portion 104 is conical (i.e. it decreases in diameter as it extends subcutaneously away from skin surface) with an angle from the vertical of between around 5 and 40 degrees.

The extracorporeal portion 106 is the part of the device that protrudes above the outer surface of the dermis. In this embodiment, the extracorporeal portion 106 has substantially cylindrical outer surface, and an inner surface forming a recess 111. A retaining cap 110 locates over the recess 111.

FIG. 2b shows the component parts of the percutaneous fluid access device 100, comprising a base portion 113 including the subcutaneous portion 102 and the percutaneous portion 104, as well as a housing 114, compression and alignment plate 112 and a retaining cap 110.

The base portion 113 includes a base and four fluid channels 115 shown most clearly in FIG. 2c. In alternative embodiments, the number of ports may vary including a single port. Each fluid channel 115 is in fluid communication with a lumen of the multi-lumen supply tube 6 shown in FIG. 2b. The supply tube 6 exits the subcutaneous portion 102 of the base portion 113 from its side and, when implanted, runs a short distance in a channel formed in the bone of the patient. At its upper end (being the end protruding from the patients head), the base portion has a recess 111 accessing the four fluid channels 115. The recess 111 is designed to accommodate the housing 114. The base portion 113 has a seal (not shown), which seals each fluid channel upon removal of the housing 114 from the base portion 113. Location features (not shown) for the associated connector device (shown in FIGS. 4a and 4b) are also provided, and a macro-alignment feature ensures the connector device is in the approximately correctly orientation prior to attachment. The location features and macro alignment feature are described in more detail below, with reference to an alternative embodiment—these features also apply to this embodiment.

The housing 114 includes internal fluid channels 115 in the base portion 113 and respective septa 116 sealing the end of each channel 115. Four individual septa 116 may be arranged with each septum 116 sealing one fluid channel 115 as shown in FIG. 2b, alternatively a single septum 115 may cover multiple or all fluid channels 115.

The retaining cap 110 has an open upper end with a lateral upper flange 123. A lower end opposing the upper end has a hole generally through the centre and cylindrical side walls depending downwardly from the open end. A compression and alignment plate 112 is located between the housing 114 and the cap, as shown in FIG. 2b. The compression and alignment plate 112 has four holes located in alignment with the fluid channels 115 through the housing 114, with which the septa 116 sealingly engage. During assembly of the percutaneous fluid access device 100, the compression and alignment plate 112 enables compression so as to ensure a seal is effectively formed between the cap 110, housing 114 and base portion 113.

Figure 4A:
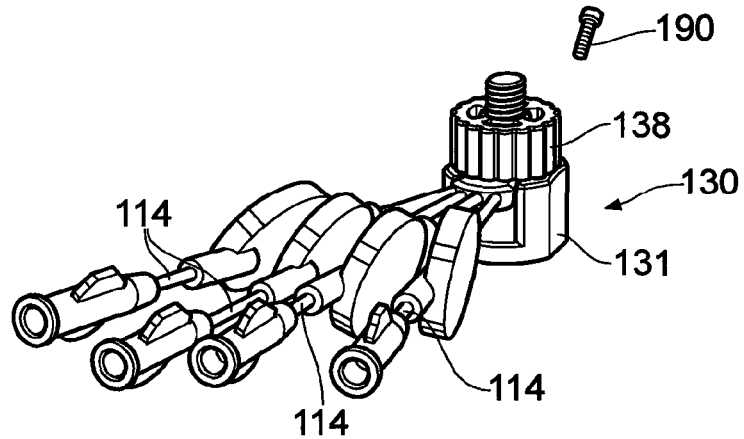
FIG. 4a is a perspective view of the connector device, with the supply tubes attached
Figure 4B:
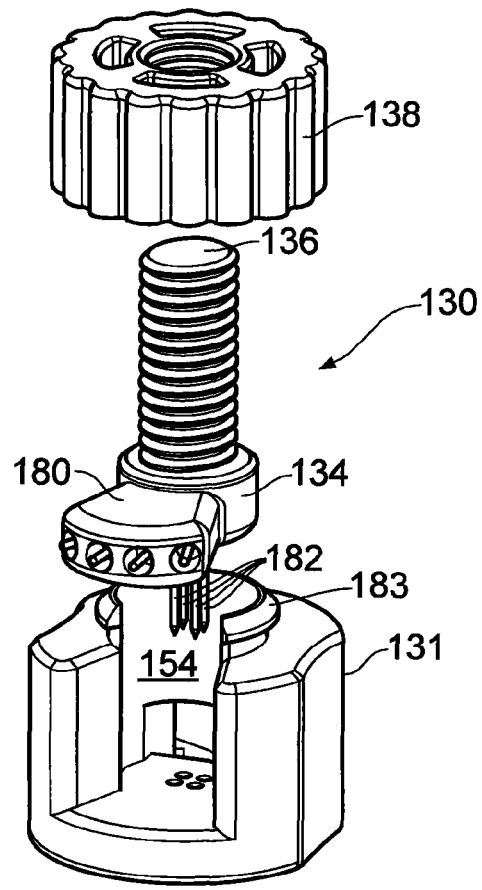
FIG. 4b is an exploded perspective view of the connector device.

FIGS. 4a and 4b provide respectively an assembled and an exploded view of the connector device 130. The connector base 131 is configured to be releaseably attachable to the percutaneous fluid access device 100.

The connector base 131 is arranged to receive a needle holder 134. The needle holder 134 comprises a substantially flat, keyhole shaped, supporting member 180. Four hollow needles 182 project perpendicularly from the flat surface of the supporting member. The four hollow needles 182 are spaced apart in a configuration that matches the arrangement of the fluid channels 115 of the percutaneous fluid access device 100. The needle holder 134 is also shaped to fit within, and slide along, a guide channel 154 of the connector base 131. The needle holder 134 also includes four internal channels that provide separate fluidic channels between the lumens of the four hollow needles 182 and the four supply tubes 14. The screw threaded shaft 136 attached to the needle holder 134 is held by the threaded inner surface of the knurled portion 138. A lip 183 protruding from the connector base 131 secures the knurled portion 138 to the base 131.

In order to lock the connector device 130 to the percutaneous fluid access device 100, the connector base 131 is first located on the percutaneous fluid access device 100. A screw 190 is inserted into an elongate aperture in the connector base and tightened so that an attachment mechanism in the connector base firmly engages a recess and grooves in the percutaneous fluid access device 100. The attachment mechanism comprises two fixed balls and a floating ball member comprising a third ball carried by a hinge (not shown in FIG. 4a). The connector device is thus locked to the percutaneous fluid access device 100 (although no fluid linkage has yet been established).

The procedure for establishing a fluid connection is then as follows:

The hollow needles 182 of the needle holder 134 are positioned above the septa 116 in alignment with the respective fluid channels 115. The connector base 131 is held in one hand whilst the other hand rotates the knurled portion 138 of the connector device 130 in an anticlockwise direction thereby driving the shaft 136 and needle holder 134 along the guide channel inside the connector base 131. This translational motion of the needle holder along the guide channel causes the four hollow needles 182 to pierce the septum or septa 116 and enter the four fluid channels 115. Holding the connector base 131 ensures no torque is applied to the device-bone connection. In this manner, the four separate fluid pathways through the percutaneous access apparatus 12 are established.

Once the required fluid delivery has occurred, the knurled portion 138 can be rotated in a clockwise direction to withdraw the four hollow needles 182 back through the septum 122. The connector device 130 can then be unlocked from the percutaneous fluid access device 100 by removing the screw 190. If required, the various components of the fluid delivery system can be MRI compatible.

During fluid delivery, hollow needles of the connector device (shown as dotted lines 120 in FIG. 2c) pierce the septa 116, enter the fluid channels 115 and thereby provide the required fluid communication with each fluid channel 115. In the absence of an attached connector device, the septa 116 provide a fluid seal for all fluid channels that prevents leakage of fluid, or ingress of unwanted material (e.g. bacteria) from the environment external to the patient's body. Air is also prevented from either entering or venting from the base portion 113.

The housing 114 also contains elongate filters 117 arranged in the fluid channels 115. In use, each needle 120 pierces through each septum 116 but stops above the filter 117. This ensures that fluid passes through the filter 117 on entering the fluid channel 115. The filter 117 may also remove loose particles of the septum 116 that may result from the needle piercing the septum 116. The filter 117 also removes any other foreign bodies that might be present, and/or any bacterial contaminant. The filter 117 traps any air present in the system and ensures that it does not pass into the fluid channel 115 and hence the fluid communication path. The filter 117 comprises a mesh containing filter material capable entrapping loose particles as well as air, bacteria etc.

The septum 116 is constructed of a resilient material, such that as the needle is removed from the septum 116, the seal to the fluid channel 115 is re-established. The septum 116 may be made of silicon or similar material.

In this embodiment, the housing 114 also comprises a profiled casing 118 arranged to contain the septa 116 and the filters 117 according to their shape. The housing 114 inserts into a recess 111 in the base portion 113 as shown in FIG. 2b. The compression and alignment plate 112 and the cap 110 assemble on to an extracorporeal surface 121 of the base portion 113. The assembly is aligned such that holes 119 in the compression and alignment plate 112, through which the needles pass, always line up with the fluid channels 115 in the base portion 113 in order to ensure the correct needle is inserted into the corresponding fluid channel and channel identification is maintained. This ensures that the correct drug is administered through the correct channel to the correct part of the brain. One or more recesses or protrusions or other alignment features in or on the base portion 113 correspond with one or more protrusions or recesses or other alignment features in or on the compression and alignment plate 112 (not shown). Alternatively, alignment may be integrated into the fixture mechanism of the cap 110 to the base portion 113, which may for example be press fitted or threaded together.

O-ring seals are provided between the housing 114 and the base portion 113. Each channel 115 into which a filter 117 is inserted has an O-ring 122. The O-ring 122 is located on the outer surface of each filter 117, between the filter and the casing 118, in order to seat at the upper part of each channel 115.

Figure 3A:
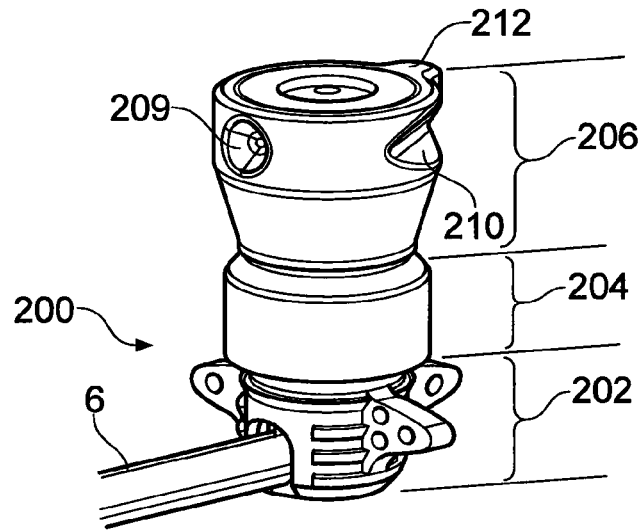
FIG. 3a is a perspective view of a further embodiment of the percutaneous fluid access device.
Figure 3B:
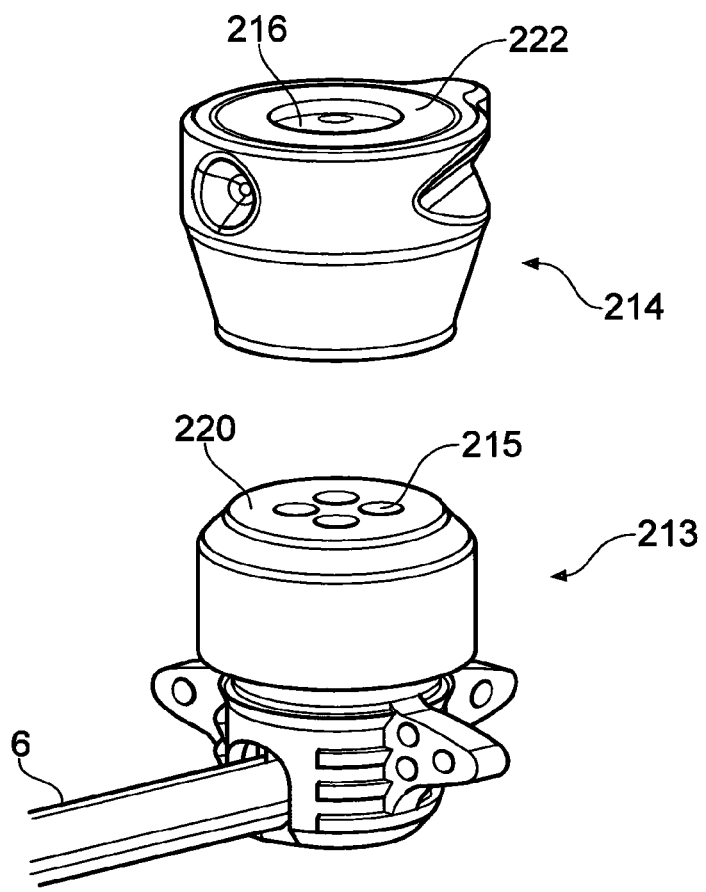
FIG. 3b shows the perspective view of the percutaneous fluid access device of FIG. 3a, with a housing separated from the base portion.

FIGS. 3a and 3b show an alternative embodiment of the percutaneous fluid access device 200. FIGS. 3a and 3b show a percutaneous fluid access device 200 comprising a subcutaneous portion 202, a percutaneous portion 204 and an extracorporeal portion 206. These portions have the same meaning as for the previous embodiment, and so are not redefined here. The subcutaneous portion 202 and the percutaneous portion 204 together form a base portion 213, the base portion 213 being the portion that locates to the patient's skull.

The base portion 213 includes four fluid channels 215. In alternative embodiments, there may be a plurality of fluid channels or a single fluid channel 215. Each fluid channel 215 is in fluid communication with a lumen of the multi-lumen supply tube 6. The supply tube 6 exits the subcutaneous portion 202 of the base portion 213 from a side of the base portion 213 and, when implanted, runs a short distance in a channel formed in the bone of the patient. In this embodiment the fluid channels 215 extend to an extracorporeal surface 220 of the base portion 213.

In this embodiment the housing 214 is extracorporeal. A septum and a filter or filters aligned with each fluid channel are located within the housing 214. The housing 214 has fluid channels 215 corresponding to the fluid channels in the base portion 213. FIGS. 3a and 3b show the upper surface (the surface connecting to the connector device) of the housing 214 comprising a cap 222. The cap 222 has a single through hole providing access to a single septum 216 to the fluid channels 215 in the housing 214. The housing 214 has a substantially cylindrical outer surface with a conical portion narrowing towards a connection surface with the corresponding extracorporeal connection surface 220 of the base portion 213.

Figure 3C:
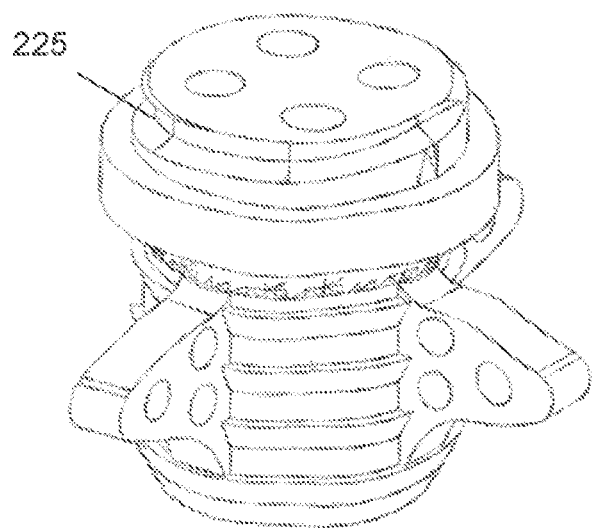
FIG. 3c is a perspective view of the base portion of FIGS. 3a and 3b showing an embodiment of an attachment mechanism by which the housing attaches to the base portion.

The housing 214 and the base portion 213 are aligned during assembly to ensure the correct needle is inserted into the corresponding channel and channel identification is maintained. This ensures that the correct drug is administered through the correct fluid channel 215 to the correct part of the brain. One or more recesses, protrusions or other alignment features (not shown) in either the base portion 213 or the housing 214 may correspond with one or more protrusions, recesses or other alignment features. Alignment may be integrated into the fixture mechanism of the housing 214 to the base portion 213, which may for example be press fitted or threaded together. FIG. 3c shows a single turn thread fixture arrangement 225 located on the extracorporeal surface 220 of the base portion 213. A second septum or seal is provided between the housing 214 and the base portion 213 to obviate ingress or egress of air or contaminants.

A conical recess 209 and two v-shaped grooves 210 are spaced apart around the circumference of the housing 214. A macro-alignment feature 212 is also provided. The conical recess 209 and grooves 210 act as very precise (kinematic) location features for the associated connector device (shown in FIGS. 4a and 4b), whilst the macro-alignment feature 212 ensures the connector device is in the approximately correctly orientation prior to attachment.

In a variant of the embodiment of the percutaneous fluid access device of FIG. 3, the base portion is entirely subcutaneous, so that the attachment surface is also subcutaneous.

Figure 5:
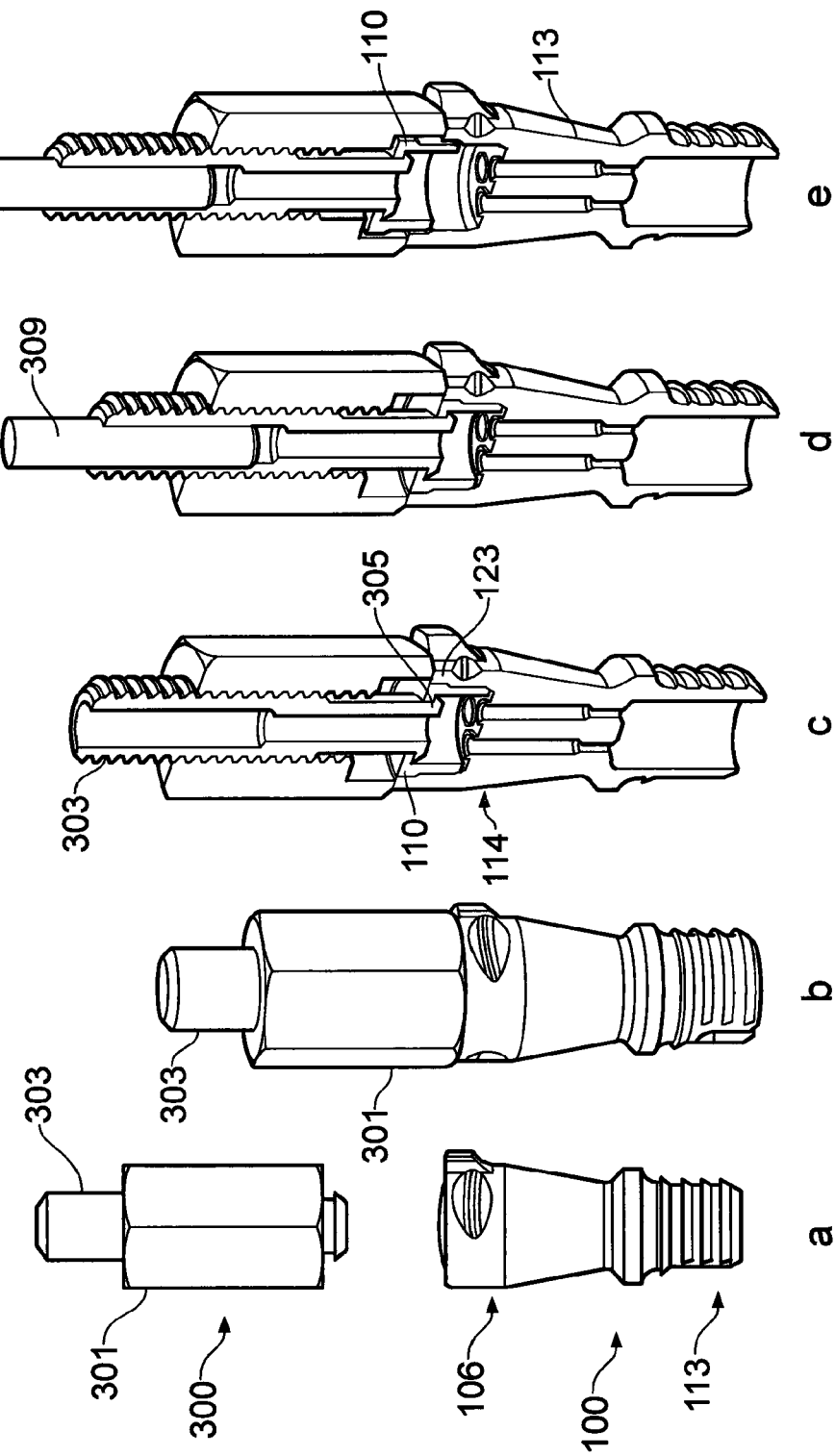
FIG. 5 shows an embodiment of the tool used to remove a housing inserted into the base portion according to the embodiment of the percutaneous fluid access device shown in FIGS. 2a to 2c, and the sequence of coupling the tool to the housing and removing the housing from a recess in the base portion.
Figure 6:
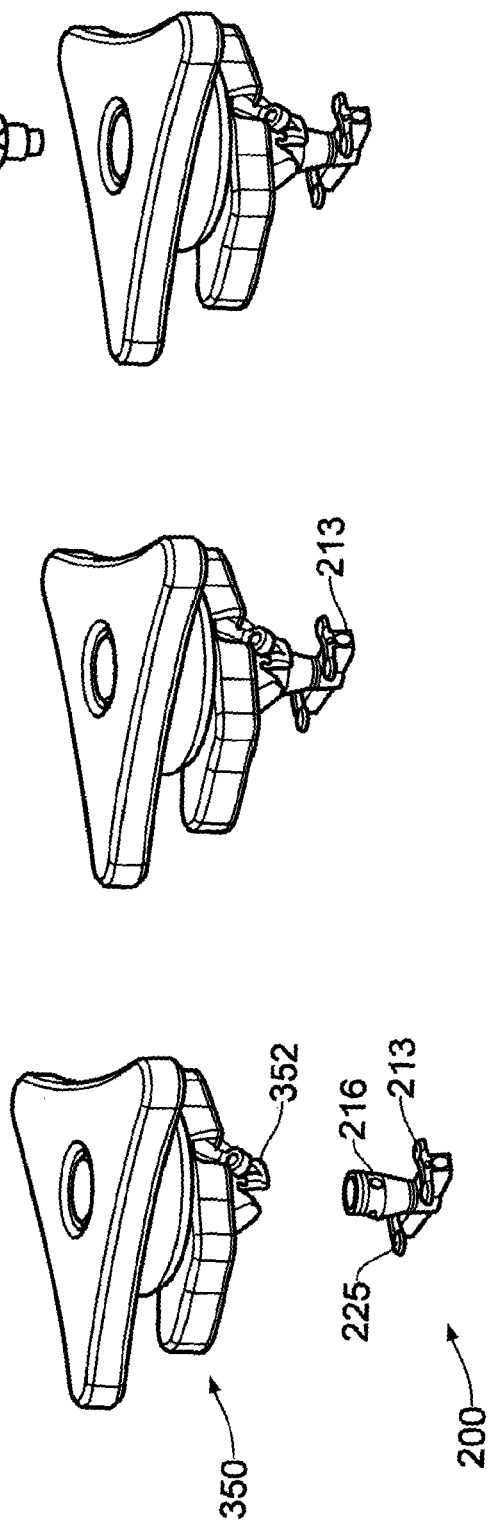
FIG. 6 shows a further embodiment of the tool used to remove a housing according to another embodiment of the percutaneous fluid access device shown in FIGS. 3a and 3b.

FIG. 5 shows an embodiment of the tool used to remove and reassemble the housing 114 from the base portion 113 of FIGS. 2a, 2b and 2c. FIG. 6 shows an embodiment of the tool used to remove and reassemble the housing 214 from the base portion 213 of FIGS. 3a and 3b.

Once the drug has been administered to the patient via the connector device 130, the needles are withdrawn from the fluid ports in the housing 114, 214 to remove fluidic connection to the base portion. The connector device 130 is then disconnected from the housing 114, 214, removal being a reversal of the connection procedure described above. Should it be determined that the septum has degraded beyond the acceptable limits of sealing, it is then required to remove the housing and replace the septum or septa, as well as any filters that be present. This procedure is carried out in an aseptic environment and does not require the patient to undergo surgery, thereby reducing risk of infection or complications as a result of surgery. For some patients, surgery may have hitherto been a repeated requirement, as successive septa degrade over the duration of the treatment.

In the embodiment of the tool 300 of FIG. 5, the cap 110 of the housing 114 is press fitted in a recess in the base portion 113 (see FIG. 5c). In this embodiment, the cap 110 is required to be removed. The removal tool 300 comprises a body 301, within which a hollow threaded tube 303 is inserted. The body 301 is placed against the rim of the base portion 113, without contacting or obstructing removal of the cap 110. The body 301 serves to brace the tool 300 so that a controlled force can be applied to remove the cap 110. The end of the tube 303 entering the cap 110 has protruding tabs 305 shown in FIG. 5c. The tabs 303 are sufficiently flexible to be able to be pushed into the cap 110 and lock underneath a corresponding lip 123 in the cap 110. FIG. 5d then shows an internal rod 309 being inserted inside the tube 303 to prevent the connection between the tabs 303 and the lip 123 from breaking during the removal process. The threaded tube 303 is then rotated to remove the tube 303 together with the cap 110 from the base portion 113, see FIG. 5e.

In the embodiment of the tool 350 of FIG. 6, the housing 214 of the percutaneous fluid access device 200 is attached to the base portion 213 via the subcutaneous surface. Note that the base portion 213 in this embodiment has plates 225, which attach to the skull of the patient. The removal or attachment tool 350 has a set of jaws 352 which clamp around the housing 214. The housing 214 is removed in this embodiment by rotating the jaws 352 within the tool 350 so as to remove the housing 214 from the base portion 213.

Once the housing 214 is removed from the base portion 213, the housing 214 is disposed of. A replacement housing can be fitted to the base portion using the tool 300, 350 according to the above embodiments. Alternative tool designs are possible, and may be necessary according to the fixture mechanism of the housing to the base portion.

Alternatively, the housing may be re-used. The degraded septum or septa may be removed from the housing and replaced. Filters that may also be present can also be replaced in the same manner. All re-used components are cleaned and sterilised before re-use.

Figure 7:
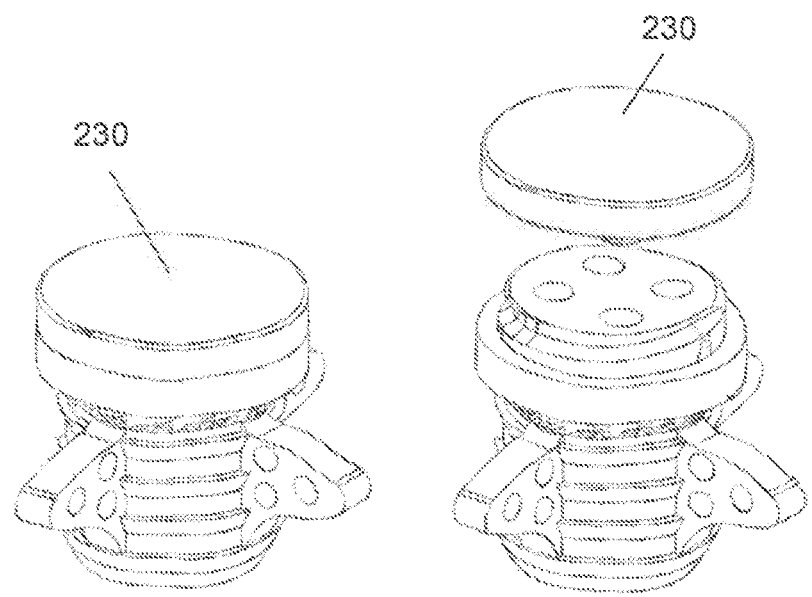
FIG. 7 is the perspective view of FIG. 3c showing a cover attached to the base portion and separated from the base portion.

Once the particular dosage has been administered, and with the housing removed from the base portion, a cover may be fitted to the surface of the base portion to provide protection to the fluid communication channel. FIG. 7 shows an exemplary cover 230.

Although the invention has been described above with reference to one or more preferred embodiments, it will be appreciated that various changes or modifications may be made without departing from the scope of the invention as defined in the appended claims. For example, one or more electrical pathways may also be provided through the housing and base portion.

The invention claimed is:

1. A percutaneous fluid access apparatus including a percutaneous fluid access device and a plurality of neurosurgical catheters implantable within a brain of a patient, the percutaneous fluid access device comprising:

a base portion including (i) a subcutaneous portion, (ii) a percutaneous portion that passes through skin of the patient, (iii) an extracorporeal surface, and (iv) a plurality of ports configured for connection to the plurality of neurosurgical catheters; and a housing comprising a plurality of fluid channels fixed in position relative to each other, at least one seal for sealing the plurality of fluid channels, and a plurality of particle filters, each fluid channel comprising one of the plurality of particle filters,
wherein the housing is removably attachable to the base portion so that (i) the housing is configured to be removed from an extracorporeal side of the plurality of ports without disturbing an interface between the skin and the percutaneous portion and (ii) when the housing is attached to the base portion, the housing is secured in place relative to the base portion,
the plurality of fluid channels are in fluid communication with the plurality of ports when the housing is attached to the base portion,
the plurality of filters and the at least one seal are contained by a casing of the housing such that, when the housing is removed from the base portion, the plurality of filters and the at least one seal are removed from the base portion along with the casing, and
when the housing is attached to the base portion, at least one of the at least one seal and the plurality of particle filters are located inside the base portion.

2. The apparatus according to claim 1, wherein the housing is removably attachable to the extracorporeal surface of the base portion.

3. The apparatus according to claim 1, wherein the base portion has a recess, and wherein the housing is adapted to be inserted into the recess through the extracorporeal surface.

4. The apparatus according to claim 1, further comprising a connector device having a plurality of fluid ducts, wherein the connector device is adapted for connection to the percutaneous fluid access device to establish fluid communication between the plurality of fluid ducts and the plurality of fluid channels.

5. The apparatus according to claim 4, wherein the connector device comprises a plurality of hollow needles.

6. The apparatus according to claim 5, wherein the plurality of hollow needles are configured to be inserted through the at least one seal to establish fluid communication between the plurality of hollow needles and the plurality of fluid channels.

7. The apparatus according to claim 1, further comprising a cover adapted to fit over the base portion when the housing is removed from the base portion.

8. The apparatus according to claim 1, further comprising a tool adapted to engage the base portion and the housing during removal and/or assembly of the housing to/from the base portion.

9. The apparatus according to claim 1, wherein at least one second seal is provided between the housing and the base portion.

10. The apparatus according to claim 9, wherein at least one third seal, which is included with the base portion, seals the plurality of ports upon removal of the housing from the base portion.

11. The apparatus according to claim 1, wherein the base portion further includes an extracorporeal portion on an extracorporeal side of the percutaneous portion.

12. The apparatus according to claim 1, wherein the at least one seal covers an extracorporeal-side opening of the plurality of fluid channels.

13. The apparatus according to claim 1, wherein at least a portion of the housing extends through the skin of the patient when the housing is attached to the base portion.

14. The apparatus according to claim 1, which is linkable to one or more supply tubes by way of an associated connector device that is releasably attachable to the percutaneous fluid access device.

15. A method of using a percutaneous fluid access apparatus comprising (1) a plurality of neurosurgical catheters implantable within a brain of a patient and (2) a percutaneous fluid access device including: (i) a base portion including a subcutaneous portion, a percutaneous portion that passes through skin of the patient, an extracorporeal surface, and a plurality of ports configured for connection to the plurality of neurosurgical catheters; and (ii) a housing comprising a plurality of fluid channels fixed in position relative to each other, at least one seal for sealing the plurality of fluid channels, and a plurality of particle filters, each fluid channel comprising one of the plurality of particle filters, wherein the housing is removably attachable to the base portion, the plurality of fluid channels are in fluid communication with the plurality of ports when the housing is attached to the base portion, the housing is secured in place relative to the base portion when the housing is attached to the base portion, the plurality of filters and the at least one seal are contained by a casing of the housing such that, when the housing is removed from the base portion, the plurality of filters and the at least one seal are removed from the base portion along with the casing, and when the housing is attached to the base portion, at least one of the at least one seal and the plurality of particle filters are located inside the base portion, the method comprising:
removing the housing from the base portion of the percutaneous fluid access device by removing the housing from an extracorporeal side of the plurality of ports without disturbing an interface between the skin and the percutaneous portion.

16. The method according to claim 15, further comprising:
disposing of the housing after removal of the housing from the base portion of the percutaneous fluid access device; and/or
attaching a replacement housing to the base portion of the percutaneous fluid access device.

* * * * *